United States Patent
Watanabe

(10) Patent No.: US 6,517,994 B2
(45) Date of Patent: Feb. 11, 2003

(54) LACTONE RING-CONTAINING (METH)ACRYLATE AND POLYMER THEREOF FOR PHOTORESIST COMPOSITION

(75) Inventor: Takeru Watanabe, Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/106,459

(22) Filed: Mar. 27, 2002

(65) Prior Publication Data

US 2002/0147291 A1 Oct. 10, 2002

(30) Foreign Application Priority Data

Apr. 10, 2001 (JP) .......................... 2001-111616

(51) Int. Cl.⁷ .................. G03F 7/004; G08F 10/00; C07D 307/00
(52) U.S. Cl. ................. 430/270.1; 430/326; 526/281; 549/300
(58) Field of Search ............... 430/270.1, 326; 526/281; 549/300

(56) References Cited

U.S. PATENT DOCUMENTS

| | | | |
|---|---|---|---|
| 6,280,898 B1 * | 8/2001 | Hasegawa et al. | 430/270.1 |
| 6,447,980 B1 * | 9/2001 | Rahman et al. | 430/270.1 |
| 6,303,266 B1 * | 10/2001 | Okino et al. | 430/270.1 |
| 6,383,713 B1 * | 5/2002 | Uetani et al. | 430/270.1 |
| 6,406,828 B1 * | 6/2002 | Szmanda et al. | 430/270.1 |
| 6,426,171 B1 * | 7/2002 | Jung et al. | 430/270.1 |
| 6,441,115 B1 * | 8/2002 | Chang et al. | 526/328.5 |

* cited by examiner

Primary Examiner—Deborah C. Lambkin
(74) Attorney, Agent, or Firm—Millen, White, Zelano & Branigan, P.C.

(57) ABSTRACT

The invention discloses a novel polymerizable (meth) acrylate ester compound having a lactone ring structure represented by the general formula

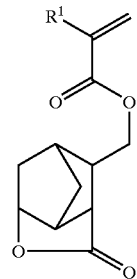

in which $R^1$ is a hydrogen atom or a methyl group. A synthetic route for the preparation of this (meth)acrylate ester compound is described. This monomeric compound can readily be polymerized into a (co)polymer which is useful as a base resinous ingredient in a chemically amplified photoresist composition having advantages in respects of high transparency to short-wavelength ultraviolet light for patterning exposure and excellent resistance against dry etching in addition to the high sensitivity, fine pattern resolution and excellent adhesion to the substrate surface.

15 Claims, No Drawings

LACTONE RING-CONTAINING (METH)ACRYLATE AND POLYMER THEREOF FOR PHOTORESIST COMPOSITION

BACKGROUND OF THE INVENTION

The present invention relates to a lactone ring-containing (meth)acrylate ester compound which is a novel compound not known in the prior art and a polymeric compound thereof as well as to a photoresist composition containing the polymer as the base resinous ingredient and a photolithographic resist patterning method by using the photoresist composition.

Along with the trend in recent years in the technology of semiconductor devices such as LSIs toward higher and higher degrees of integration and higher and higher working velocities, the technology of photolithographic resist patterning is continuedly required to accomplish further upgrading in respect of fineness of resist patterning to meet the modern pattern design rule. As is generally understood, ultrafine patterning of a resist layer having a fineness of as fine as 0.3 μm or even finer required in the next-generation technology can be accomplished by the so-called deep ultraviolet photolithography using ultraviolet light of a very short wavelength such as KrF excimer laser beams, ArF excimer laser beams and the like as the patterning exposure light although such an ultrafine resist patterning technology is still under development.

It is of course that the photoresist composition used in such a deep UV photolithographic process by using excimer laser beams or, in particular, ArF excimer laser beams of 193 nm wavelength as the patterning exposure light is required to have very high transparency to the light of the wavelength. In addition, the requirements for the photoresist composition include high etching resistance to withstand etching even with a decreased thickness of the resist layer, high sensitivity to the exposure light to decrease the load on the expensive optical system for exposure and, inter alia, high pattern resolving power in order to give a patterned resist layer having high fidelity to the extremely fine photomask pattern. In order to satisfy all of these requirements, the photoresist composition must be formulated by using a film-forming base resin having high transparency to the exposure light, high rigidity and high reactivity in combination. Although a variety of proposals and attempts have been made to obtain such a resinous compound, none of the resinous compounds known in the art can meet these requirements and none of the currently available photoresist compositions are suitable for use in the deep UV photolithographic process.

Examples of known resinous polymeric compounds having high transparency to the deep UV light include copolymers of a monomer mixture containing an acrylic or methacrylic acid derivative and polymers having monomeric units derived from an aliphatic cyclic compound originating in a norbornene compound. None of these polymeric compounds, however, can satisfy all of the requirements for the resinous ingredient in a photoresist composition for the deep UV photolithographic patterning technology. For example, while it is a relatively easy matter to obtain a (meth)acrylic acid derivative-based copolymeric resin having high reactivity because the copolymer is susceptible to the introduction of highly reactive monomeric units or to the increase of acid-dissociable solubility-reducing substituent groups, the main chain structure of the resin molecules renders it extremely difficult to enhance rigidity of the resin. On the other hand, the polymeric resin having an alicyclic monomeric structure in the main chain is satisfactory in respect of rigidity but the reactivity with an acid cannot be high enough as compared with the (meth)acrylate-based copolymeric resins and the reactivity cannot be increased easily due to the low versatility in polymerization.

In addition, the hydrophobicity of the main chain structure thereof is so high that adhesion of the photoresist layer to the substrate surface cannot be strong enough. Accordingly, a photoresist composition prepared by using these resins as the base resin cannot simultaneously satisfy the requirements for the sensitivity, pattern resolution and etching resistance. Namely, some of the photoresist compositions are acceptable in respect of the sensitivity and pattern resolution but unacceptably poor in respect of the etching resistance while the others exhibit good etching resistance but are poor in the sensitivity and pattern resolution.

SUMMARY OF THE INVENTION

Accordingly, the primary object of the present invention completed in view of the above described problems and disadvantages in the prior art is to provide a novel and improved photoresist composition suitable for use in the deep UV photolithographic resist patterning process by using UV light having a wavelength of 300 nm or shorter or, in particular, ArF excimer laser beams of 193 nm wavelength as the patterning exposure light as well as a deep UV photo-lithographic resist patterning method by using the improved photoresist composition. The secondary object of the present invention is to provide a novel polymeric resinous compound suitable for use as a base resin ingredient in the photoresist composition for the deep UV photolithographic resist patterning method as well as a novel monomeric compound from which the aforementioned resinous compound can be prepared by polymerization.

Thus, firstly, the monomeric compound provided by the present invention, which is a novel compound not known in the prior art or not described in any literatures, is 3-(meth)acryloyloxymethyl-2,6-norbornane carbolactone as a norbornyl (meth)acrylate ester compound having a lactone ring structure as represented by the general formula (1) below;

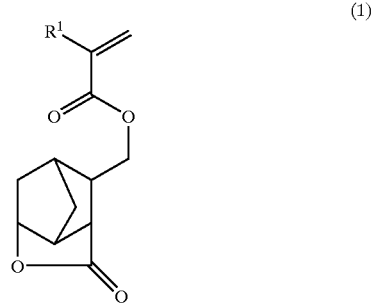

(1)

in which $R^1$ is a hydrogen atom for the acrylate compound or a methyl group for the methacrylate compound.

Secondly, the present invention provides a novel polymeric compound suitable as the base resinous ingredient in a deep UV photoresist composition, which consists of recurring monomeric units, forming the main chain structure, comprising the units represented by the general formula (1a) below:

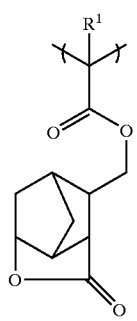

(1a)

in which $R^1$ is a hydrogen atom or a methyl group, and preferably having a weight-average molecular weight in the range from 2000 to 100000 when the intended application thereof is as a base resin in a photoresist composition.

Thirdly, the present invention provides a copolymeric resinous compound suitable for use as a base resin in a deep UV photoresist composition, comprising two types of recurring monomeric units in combination including the monomeric units of the first type represented by the above given general formula (1a) and monomeric units of the second type represented by the general formula (2a) below:

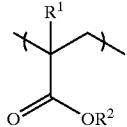

(2a)

in which $R^1$ has the same meaning as defined above and $R^2$ is a tertiary alkyl group or tertiary cycloalkyl group having 4 to 20 carbon atoms.

Fourthly, the present invention provides a novel photoresist composition suitable for the deep UV photolithographic resist patterning process, which comprises, as a uniform solution:

(A) a base resin which is a polymer comprising the recurring monomeric units represented by the above given general formula (1a) or a copolymer comprising two types of the recurring monomeric units represented by the above given general formulas (1a) and (2a);

(B) a radiation-sensitive acid-generating compound; and (C) an organic solvent as a solvent for the components (A) and (B).

Fifthly, the present invention provides a novel deep UV photolithographic resist patterning method which comprises the steps of:

i) coating a substrate with the above defined photoresist composition in the form of a solution to form a coating layer of the solution;

ii) drying the coating layer to form a dried photoresist layer on the substrate surface;

iii) patternwise exposing the dried photoresist layer to ultraviolet light having a wavelength not exceeding 300 nm;

iv) optionally, subjecting the photoresist layer to a post-exposure baking treatment; and v) developing the photoresist layer with an aqueous alkaline solution to patternwise dissolving away the photoresist layer.

DETAILED DESCRIPTION OF THE PREFERRED EMBODIMENTS

In the following, the various aspects of the present invention are described in detail starting with the synthetic preparation of the monomeric norbornyl (meth)acrylate compound having a lactone ring structure in the molecule represented by the general formula (1) given above.

The specific norbornyl (meth)acrylate compound represented by the above given general formula (1) can be synthetically prepared most conveniently by way of the three-step synthetic route described below though not particularly limitative to this route.

In the first step reaction of the synthetic route, the starting reactant is 5-norbornene-2,3-dicarboxylic acid of the formula (3) below or 5-norbornene-2,3-dicarboxylic acid anhydride of the formula (4) below. The starting compound, e.g., the dicarboxylic acid compound (3), is dissolved in a solvent and the solution is heated in the presence of an acid catalyst to form the norbornyl carboxylic acid compound having a lactone ring structure of the formula (5) according to the following reaction scheme (I).

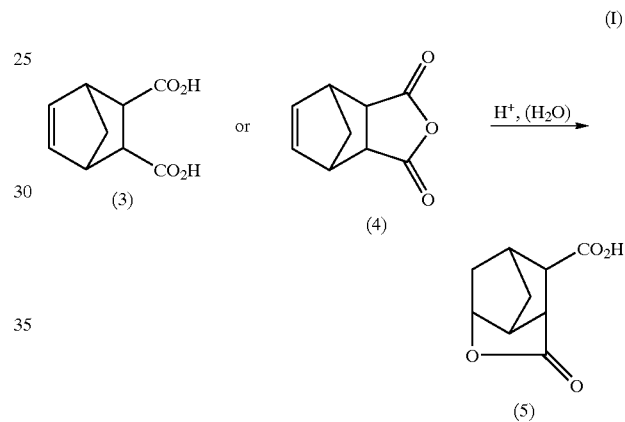

(I)

The acid catalyst used in the above mentioned first step lactone ring-forming reaction of the reaction scheme (I) can be selected, though not particularly limitative, from the group consisting of inorganic acids such as sulfuric acid, nitric acid and hydrochloric acid as well as salts thereof, organic acids such as formic acid, acetic acid, trifluoroacetic acid, p-toluenesulfonic acid and methanesulfonic acid as well as salts thereof and cation-exchange resins. The amount of the acid catalyst contained in the reaction mixture is in the range from 0.001 mole to 10 moles or, preferably, from 0.01 mole to 2 moles per mole of the starting reactant (3) or (4).

The solvent used for the preparation of the reaction mixture in the first step reaction is selected, though not particularly limitative, from the group consisting of organic acids such as acetic acid, hydrocarbon compounds such as toluene, xylene and heptane, ethers such as dibutyl ether and diethyleneglycol diethyl ether and chlorinated hydrocarbon compounds such as methylene chloride and 1,2-dichloroethane and water. These solvents can be used either singly or as a mixture of two kinds or more.

The reaction temperature of the first step reaction is not particularly limitative and can be selected in a wide range depending on other reaction conditions. It is convenient, however, that the reaction temperature is set in the range from room temperature to the vicinity of the boiling point of the reaction solvent used. When sulfuric acid is used as the acid catalyst, for example, the reaction is carried out preferably at a temperature in the range from 80 to 120° C. Though dependent on various reaction conditions, the above described lactone ring-forming reaction is complete usually within 1 to 20 hours. It is desirable in order to accomplish a highest yield of the reaction product under time saving that proceeding of the reaction is monitored by periodically subjecting a small portion of the reaction mixture to a thinlayer chromatographic analysis or gas chromatographic analysis.

In the case where the starting reactant is 5-norbornene-2,3-dicarboxylic acid anhydride (4), in particular, it is necessary that water is added to the reaction mixture in an at least equimolar amount relative to the starting anhydride in order to hydrolyze the anhydride into the dicarboxylic acid compound. The reaction is conducted by heating the reaction mixture under agitation in an atmosphere of an inert gas such as nitrogen. After completion of the reaction, the reaction mixture is subjected to an aqueous work-up treatment or the precipitates formed in the reaction mixture are collected by filtration to give the reaction product which is the compound expressed by the formula (5) in the reaction scheme (I). Although the thus obtained reaction product has a sufficiently high purity relative to the compound (5) to be usable as such in the next step reaction, it is optional, if necessary, that the reaction product is subjected to a purification treatment by a conventional purification procedure such as recrystallization and chromatographic methods.

The second step reaction to follow the above described first step reaction is a reducing reaction expressed by the reaction scheme (II) given below in which the monocarboxylic acid compound of the formula (5) obtained in the first step reaction is reacted with a reducing agent into the corresponding hydroxyl compound of the formula (6). The reaction is carried out usually by dissolving the starting carboxylic acid compound (5) in a solvent and the reactant is reacted with a reducing agent therein.

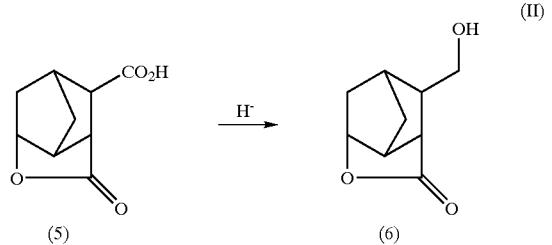

The aforementioned reducing agent used in the reducing reaction can be selected from metal hydride compounds such as diisobutylaluminum hydride, metal hydride complexes such as lithium aluminum hydride and sodium tetrahydroborate and borane reagents such as borane and borane/tetrahydrofuran complexes, of which the borane reagents are preferable in respect of the high yield of the reaction product. The amount of the reducing agent used in the reaction depends on the kind of the reducing agent but, when a borane/tetrahydrofuran complex is used as the reducing agent, for example, the amount of the reducing agent is in the range from 0.5 to 5.0 moles or, preferably, from 1.0 to 2.0 moles per mole of the starting carboxylic acid compound (5).

Though dependent on the reducing agent used, it is usual that the reducing reaction in the second step is carried out at a temperature in the range from −78° C. to 100° C. or, preferably, from 0° C. to 60° C. Though dependent on various factors, the reaction is complete usually within 1 to 20 hours. It is desirable that the end point of the reaction is determined under monitoring by periodically analyzing a small portion of the reaction mixture by the thin-layer chromatographic method or gas chromatographic method. After completion of the reaction, the reaction mixture is subjected to an aqueous work-up treatment to obtain the reaction product which is the hydroxyl-containing compound of the formula (6). It is optional according to need that the thus obtained reaction product is subjected to a purification treatment by a known method such as chromatographic and recrystallization methods.

The third step reaction to follow the above described second step reaction is the so-called (meth)acrylation reaction to form a (meth)acrylic acid ester compound (1) of the hydroxyl compound (6) as expressed by the reaction scheme (III), in which $R^1$ is a hydrogen atom or a methyl group. The method for the (meth)acrylation reaction of the hydroxyl compound (6) can be conventional including the method of using (meth)acrylic acid chloride in combination with a basic compound, direct esterification method of the hydroxyl compound (6) with (meth)acrylic acid in the presence of an acid catalyst and the dehydrating-condensation reaction of the hydroxyl compound (6) with (meth)acrylic acid by utilizing a dehydrating-condensing agent such as dicyclohexyl carbodiimide. The thus obtained (meth)acrylate compound (1) can be purified by a conventional purification procedure such as chromatographic, distillation and recrystallization methods.

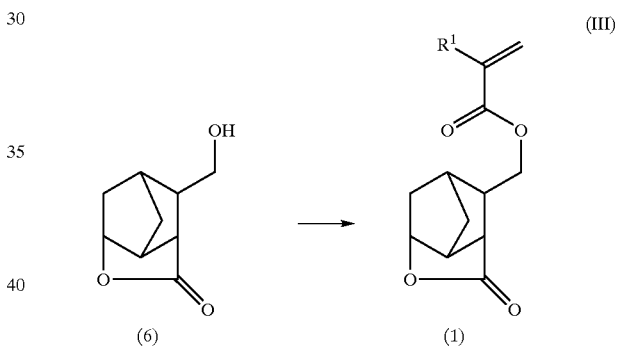

The (meth)acrylate ester compound of the formula (1) obtained in the above described manner is a novel compound not known in the prior art nor described in any literatures. This (meth)acrylate compound can readily be polymerized into a polymer comprising the recurring monomeric units represented by the general formula (1a) given before. This polymeric compound is useful as a film-forming resinous base ingredient in a photoresist composition when the weight-average molecular weight thereof is in the range from 2000 to 100000.

The base resin ingredient in the photoresist composition according to the present invention is a copolymer comprising two types of the monomeric units including those of the general formula (1a) and those of the general formula (2a) given before, optionally, in combination with further monomeric units of one or more types other than (1a) and (2a).

In the above given general formula (2a) for the monomeric units of the second type, $R^1$ is a hydrogen atom or a methyl group and $R^2$ is a tertiary alkyl or tertiary cycloalkyl group having 4 to 20 carbon atoms. Examples of the group denoted by $R^2$ include, though not particularly limitative thereto, tert-butyl, tert-pentyl, 1-ethyl-1-methylpropyl, triethylcarbinyl, 1-methylcyclopentyl, 1-ethylcyclopentyl, 1-cyclopentyl-cyclopentyl, 1-cyclohexylcyclopentyl, 1-methylcyclohexyl, 1-ethylcyclo-hexyl, 1-cyclopentylcyclohexyl, 1-cyclohexylcyclopentyl, 2-methyl-2-norbornyl, 2-ethyl-2-norbornyl, 8-methyl-8-tricyclo[5.2.1.0$^{2,6}$]decyl, 8-ethyl-8-tricyclo[5.2.1 .0$^{2,6}$] decyl, 2-methyl-2-adamantyl, 2-ethyl-2-adamantyl and 1-adamantyl-1-methyl ethyl groups. The group $R^2$ in the monomeric units of the second type (2a) is eliminable by interaction with an acid to form a carboxylic acid —COOH so that the polymer is imparted with increased solubility in an aqueous alkaline developer solution.

In addition to the above described two types of the monomeric units (1a) and (2a), the base resin ingredient in the inventive photoresist composition can be a ternary or higher copolymer by comprising one or more of other types of monomeric units which can be derived from a monomeric compound having a polymerizable double bond. Examples of such additional monomeric compounds include α, β-unsaturated carboxylic acids such as (meth)acrylic acid, esters of α, β-unsaturated carboxylic acids such as esters of (meth)acrylic acid, crotonic acid and maleic acid, α, β-unsaturated nitrites such as acrylonitrile, α, β-unsaturated lactones such as 5,6-dihydro-2H-pyran-2-one, maleic anhydride, itaconic anhydride, maleimide compounds, norbornene compounds, tetracyclo[4.4.0.1$^{2,5}$.1$^{7,10}$]dodecene compounds, allyl ether compounds, vinyl ethers and vinyl esters.

The polymeric resin according to the present invention can be prepared by conducting a polymerization reaction of the (meth)acrylate ester compound of the general formula (1), optionally, in combination with a comonomer from which the monomeric units of the general formula (2a) are derived and one or more of the above named additional comonomers. The type of the (co)polymerization reaction is not limitative and can be conventional including the radical polymerization, anionic polymerization and cationic polymerization. It is preferable that, when the thus prepared (co)polymeric resin is used as a base resin in a photoresist composition, the weight-average molecular weight of the (co)polymer is in the range from 2000 to 100000. When the weight-average molecular weight of the resin is too low, the resin may be poorly film-forming and the patterned resist layer of the photoresist composition suffers a decrease in the pattern resolution while the pattern resolution is also decreased when the weight-average molecular weight of the resin is too high.

The component (B) contained in the photoresist composition according to the present invention in combination with the above described base resin compound as the component (A) is a radiation-sensitive acid-generating agent which can be decomposed and generate an acid when irradiated with ultraviolet light of 300 nm or shorter wavelength or electron beams having an energy corresponding thereto.

A variety of radiation-sensitive acid-generating compounds have been proposed and are under actual use as an essential ingredient in a chemically amplified photoresist composition. Needless to say, the acid-generating compound is required to be soluble in an organic solvent for dissolving the base resin compound as the component (A) in order to give a photoresist composition in the form of a uniform solution suitable for the coating works to give a uniform coating film of the composition on the substrate surface.

Examples of the acid-generating compounds as the component (B) in the photoresist composition according to the present invention include triphenylsulfonium salt compounds such as triphenylsulfonium trifluoromethanesulfonate and diphenyliodonium salt compounds such as di-p-tert-butylphenyliodonium trifluoromethanesulfonate as well as other types of various onium salt compounds, alkylsulfonic acid compounds, dialkylsulfonyl diazomethane compounds, disulfone compounds and sulfonic acid imides, though not particularly limitative thereto. These acid-generating compounds can be used either singly or as a combination of two kinds or more.

The amount of the acid-generating compound as the component (B) in the inventive photoresist composition is in the range from 0.2 to 50 parts by weight or, preferably, from 0.5 to 40 parts by weight per 100 parts by weight of the base resin compound as the component (A). When the amount thereof is too small, the amount of the acid generated by exposure of the photoresist layer to light is naturally so small that the photoresist composition suffers a decrease in the sensitivity and pattern resolution while, when the amount is too large, a decrease is caused in the transparency of the photoresist composition to the exposure light also leading to an eventual decrease in the pattern resolution of the resist layer.

The component (C) of the inventive photoresist composition is an organic solvent which is not particularly limitative provided that the above described components (A) and (B) as well as other optional additives can be dissolved therein to give a uniform solution. Examples of suitable organic solvents include ketones such as cyclohexanone, alcohols such as 1-methoxy-2-propanol and 1-ethoxy-2-propanol, polyhydric alcohols and derivatives thereof such as monomethyl and monoethyl ethers of ethyleneglycol and propyleneglycol and dimethyl ethers of propyleneglycol and diethyleneglycol, propyleneglycol monomethyl ether acetate and propyleneglycol monoethyl ether acetate and esters such as ethyl lactate, butyl acetate, methyl 3-methoxypropionate and ethyl 3-ethoxypropionate. These organic solvents can be used either singly or as a mixture of two kinds or more. Particularly preferable among the above named organic solvents are diethyleneglycol dimethyl ether, 1-ethoxy-2-propanol and ethyl lactate in respect of the highest dissolving power to the acid-generating compound as the component (B) and propyleneglycol monomethyl ether acetate and mixtures thereof in respect of safety to the environment and workers' health.

While the photoresist composition according to the present invention comprises, as the essential ingredients, (A) the polymeric resin, (B) the acid-generating agent and (C) the organic solvent each described above, it is optional that the photoresist composition is additionally admixed according to need with a variety of known additives including solubility-reducing agents, acidic compounds, basic compounds, stabilizers, coloring agents, surface active agents and others each in a limited amount.

The present invention also provides a novel method for the formation of a patterned resist layer on a substrate surface. In conducting the photolithographic pattern-forming method, firstly, a substrate such as a semiconductor silicon wafer is coated with the above described photoresist composition by using a spinner or other suitable coating machine in a coating amount to give a coating layer having a thickness of 0.3 to 2.0 μm as dried and the coating layer is subjected to a prebaking treatment on a hot plate at a temperature of from 60 to 150 ° C. for 1 to 10 minutes or, preferably, from 80 to 130° C. for 1 to 5 minutes to form a dried photoresist layer which is then subjected to patternwise exposure to a radiation. The radiation for patterning exposure can be selected from high-energy electromagnetic waves such as deep ultraviolet light, excimer laser beams, X-rays and others and electron beams. The exposure dose by the radiation is in the range from 1 to 200 mJ/cm² or, preferably, from 10 to 100 mJ/cm². The thus light-exposed photoresist layer on the substrate is then subjected optionally to a post-exposure baking (PEB) treatment on a hot plate at a temperature of from 60 to 150° C. for 1 to 5 minutes or, preferably, from 80 to 130° C. for 1 to 3 minutes followed by a development treatment with an aqueous alkaline developer solution such as an aqueous solution of tetramethylammonium hydroxide in a concentration of 0.1 to 5% by weight or, preferably, 2 to 3% by weight taking 0.1 to 3 minutes or, preferably, 0.5 to 2 minutes. The development treatment can be carried out by the dipping development method, puddle development method or spray development method to patternwise dissolve away the photoresist layer so that a patterned resist layer is left on the substrate surface. The above described resist-patterning method is particularly suitable when extremely fine resist patterning, which can be accomplished by keeping various process parameters within the above specified ranges, is desired by using a high-energy patterning radiation such as deep ultraviolet light or excimer laser beams of 248 to 193 nm wavelength, X-rays or electron beams.

In the following, the various aspects of the present invention are described in more detail by way of Examples, which, however, never limit the scope of the invention in any way.

EXAMPLE 1

A synthetic procedure was undertaken according to the reaction scheme (IV) given below for the preparation of 3-methacryl-oyloxymethyl-2,6-norbornane carbolactone of the structural formula (10) which is the lactone ring-containing (meth)acrylate compound of the invention represented by the general formula (1) where R¹ is a methyl group.

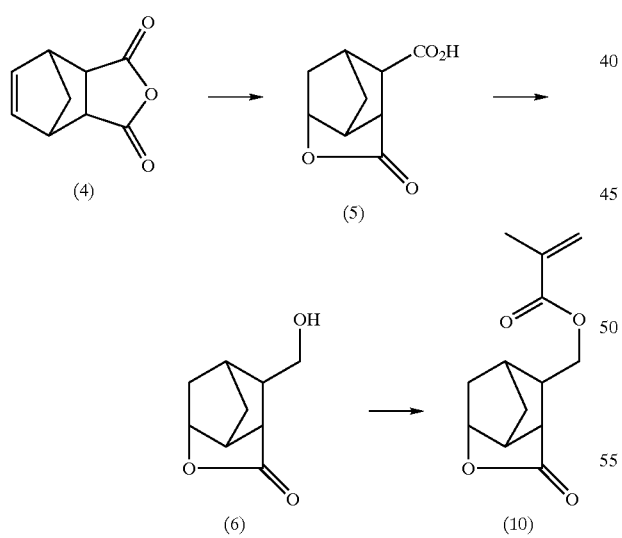

(IV)

(4)

(5)

(6)

(10)

Thus, a mixture of 50 g of 5-norbornene-2,3-dicarboxylic acid anhydride expressed by the formula (4) and 200 g of 30% sulfuric acid was agitated for 2 hours at 120° C. under an atmosphere of nitrogen gas and the precipitates formed in the reaction mixture were collected by filtration, washed with water and dried under reduced pressure to give 48 g of 2,6-norbornane carbolactone-3-carboxylic acid of the formula (5).

The entire amount of the thus obtained compound (5) was dissolved in 200 ml of tetrahydrofuran and the solution was admixed with 400 ml of a 1 mole/liter tetrahydrofuran solution of borane as a borane/tetrahydrofuran complex to be agitated for 10 hours at room temperature. After completion of 10 hours agitation, the reaction mixture was admixed with a saturated aqueous solution of sodium chloride to terminate the reaction followed by phase separation to take the organic phase which was dried over anhydrous sodium sulfate. The dried organic phase solution was subjected to removal of the solvent by evaporation under reduced pressure to give 44 g of 3-hydroxymethyl-2,6-norbornane carbolactone of the formula (6).

A mixture of 44 g of the above obtained hydroxyl compound (6), 38 g of triethylamine and 200 ml of methylene chloride was cooled to 5 to 10° C. and admixed with 32 g of methacryloyl chloride followed by agitation of the mixture for 2 hours at this temperature. After termination of the reaction by the addition of water, the reaction mixture was subjected to extraction of the organic matter with ethyl acetate. The thus obtained organic solution was subjected to concentration under reduced pressure to give a crude product which was subjected to chromatographic purification through a silica gel column to give 50 g of 3-methacryloyloxymethyl-2,6-norbornane carbolactone expressed by the formula (10), which could be identified from the analytical data shown below, as the final product. The yield of this compound was 70% of the theoretical value relative to the starting dicarboxylic acid anhydride compound of the formula (4).

Infrared absorption spectroscopic data: IR absorption peaks at 2964, 2883, 1768, 1714, 1637, 1456, 1354, 1325, 1308, 1173, 1105,1051,1020, 995, 976 and 947 cm⁻¹.

H-NMR data (δ, ppm, at 270 MHz, in CDCl₃): 1.55–1.75 (3H, m); 1.84 (1H, dd, J=14.6, 3.0 Hz); 1.93 (3H, br, s); 2.40–2.55 (2H, m); 2.65 (1H, dd, J=14.3, 4.9 Hz); 3.25 (1H, m); 4.21 (1H, dd, J=11.7, 8.8 Hz); 4.36 (1H, dd, J=11.7, 6.3 Hz); 4.78 (1H, dd, J=7.8, 4.9 Hz) 5.56 (1H, m); and 6.11 (1 H, br, s).

EXAMPLE 2

3-Acryloyloxymethyl-2,6-norbornane carbolactone of the formula (11) given below, which is the inventive lactone ring-containing (meth)acrylate compound of the general formula (1) where R¹ is a hydrogen atom, was synthetically prepared in substantially the same manner as in Example 1 excepting for the replacement of the methacryloyl chloride with the same molar amount of acryloyl chloride. The yield of the product compound (11) was 66% of the theoretical value relative to the starting dicarboxylic acid anhydride (4).

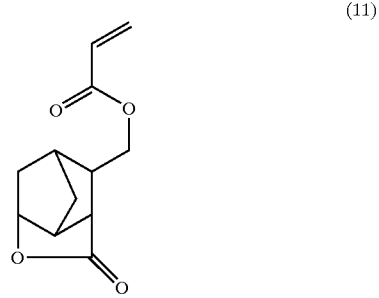

(11)

EXAMPLE 3

A binary copolymeric resin consisting of two types of monomeric units as expressed by the formula (12) below was prepared in the following manner.

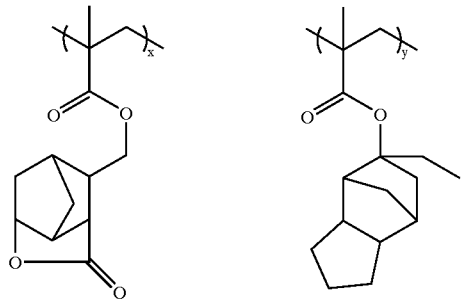

(12)

Thus, 11.8 g of the methacrylate compound (10) prepared in Example 1, 12.4 g of 8-methyl-8-tricyclo[5.2.1.0$^{2.6}$]decyl methacrylate and 60 mg of N,N'-azobisisobutyronitrile as a radical polymerization initiator were dissolved in 100 ml of tetrahydrofuran to give a polymerization mixture which was agitated for 20 hours at 60° C. under an atmosphere of nitrogen gas to effect copolymerization of the two monomeric compounds. After cooling to room temperature, the polymerization mixture was added dropwise into 2 liters of methyl alcohol under vigorous agitation and the precipitates of the copolymeric resin were collected by filtration, washed with methyl alcohol and dried under reduced pressure to give 13.3 g of the copolymeric resin as the product corresponding to 55% yield of the theoretical value. The copolymeric resin consisted of two types of recurring monomeric units as expressed by the unit formula (12) given above, in which the substrasts x and y each had a value corresponding to a 50:50 copolymerization ratio of the respective types of the monomeric units as calculated from the integral ratio of the $^1$H-NMR spectral data. This copolymer product had a weight-average molecular weight of 10200 with reference to polystyrenes and the molecular weight dispersion, i.e. the ratio of Mw:Mn, in which Mw is the weight-average molecular weight and Mn is the number-average molecular weight, was 1.78.

EXAMPLE 4

A ternary copolymeric resin consisting of three types of different monomeric units shown by the formula (13) below was prepared in substantially the same polymerization procedure as in Example 3 except that the comonomer mixture consisted of the methacrylate compound (10) prepared in Example 1, 2-ethyl-2-adamantyl methacrylate and 2-hydroxyethyl methacrylate in a molar proportion of 4:5:1 in place of the binary comonomer mixture used in Example 3. The yield of the copolymer product was 52% of the theoretical value. The copolymer had a weight-average molecular weight of 11000 with a molecular weight dispersion Mw:Mn of 1.85. The substrasts x, y and z in the formula (13) had values of 0.4, 0.5 and 0.1, respectively, corresponding to the molar fractions of the respective types of the monomeric units.

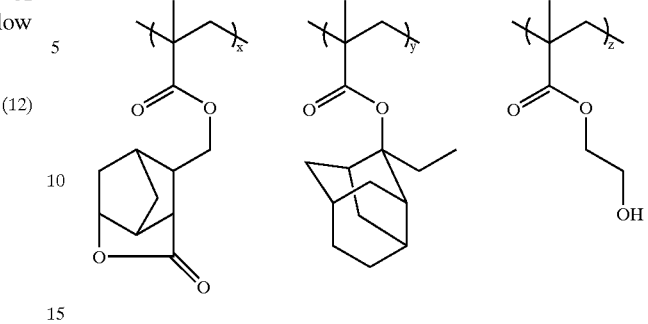

(13)

EXAMPLE 5

A photoresist solution was prepared by dissolving, in 480 parts by weight of propyleneglycol monomethyl ether acetate, 80 parts by weight of the copolymeric resin prepared in Example 3 as the base resin, 1.0 part by weight of triphenylsulfonium trifluoromethanesulfonate as the acid-generating agent and 0.08 part by weight of tributylamine to give a solution which was filtered through a Teflon membrane filter of 0.2 μm pore diameter. A semiconductor silicon wafer provided with a coating layer of hexamethyl disilazane formed by spraying the disilazane compound at 90° C. for 40 seconds was spincoated with the above prepared photoresist solution followed by a heat treatment at 110° C. for 90 seconds to form a photoresist layer of 500 nm thickness on the substrate surface. The photoresist layer was patternwise exposed to ArF excimer laser beams followed by a postexposure baking treatment at 110° C. for 90 seconds and then to a dipdevelopment treatment in a 2.38% by weight aqueous solution of tetramethylammonium hydroxide at 23° C. taking 60 seconds to give a 1:1 line-and-space patterned resist layer which was examined by using an top-down scanning electron microscope to find that good pattern resolution could be accomplished down to the 0.17 μm line pattern without pattern falling.

The same resist patterning test as above was repeated by using the ternary copolymer prepared in Example 4 as the base resin in place of the binary copolymer prepared in Example 3. The result of the test was that good pattern resolution could be accomplished down to the 0.18 μm line pattern without pattern falling. These results obtained by using the two different copolymers according to the invention well support the conclusion that the photoresist composition of the invention exhibits excellent adhesion to the substrate surface and high resolution of resist patterning.

EXAMPLE 6

Evaluation was made in the following manner of the transparency of the inventive polymeric resins to the exposure light. Thus, a 1.0 g portion of the copolymeric resin prepared in Example 3 was dissolved in 6.0 g of cyclohexanone to give a solution which was filtered through a Teflon membrane filter of 0.2 μm pore diameter. A fused silica glass plate was spin-coated with the thus prepared resin solution followed by drying at 90° C. for 60 seconds to form a thin resin film of 500 nm thickness on the substrate. The light transmission of this resin film was 80% at a wavelength of 193 nm as determined on a spectrophotometer. The same transmission measurement was undertaken for the copolymeric resin prepared in Example 4 to obtain 82% transmission for the thickness of 500 nm at the same wavelength.

These results well support the conclusion that the inventive polymeric resins have sufficiently high transparency to deep ultraviolet light for use as a base resin in a photoresist composition suitable for patterning with excimer laser beams.

EXAMPLE 7

The polymeric resin of the present invention was subjected to an evaluation test of etching resistance in the following manner. Thus, a 2 g portion of the resin was dissolved in 10 g of cyclohexanone to give a solution which was filtered through a Teflon membrane filter of 0.2 µm pore diameter. A semiconductor silicon wafer was spin-coated with the thus prepared resin solution followed by heating at 90° C. for 60 seconds to form a thin resin film of 700 nm thickness on the substrate. This resin film was subjected to the measurement of etching rate by active ion etching with a power output of 100 watts under a pressure of 5 Pa at a 30 ml/minute flow rate of carbon tetrafluoride gas to obtain a relative etching rate of 1.13 as normalized for a novolak resin as the reference resin of 1.00 relative etching rate. For comparison, the same measurement as above was undertaken for a poly(p-hydroxystyrene) resin as a conventional base resin in photoresist compositions for KrF excimer laser beam exposure to find a relative etching rate of 1.20. These results support the conclusion that the polymeric resin of the present invention is highly resistant against etching with carbon tetrafluoride gas to exhibit a relatively small etching rate.

What is claimed is:

1. A norbornyl (meth)acrylate compound having a lactone ring structure in the molecule represented by the general formula

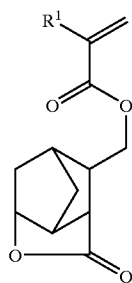

in which $R^1$ is a hydrogen atom or a methyl group.

2. A polymeric resin which consists of recurring monomeric units comprising the units of a first type represented by the general formula

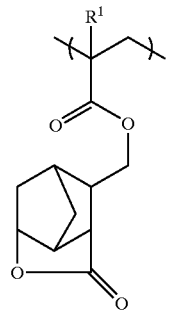

in which $R^1$ is a hydrogen atom or a methyl group.

3. The polymeic resin as claimed in claim 2 which has a weight-average molecular weight in the range from 2000 to 100000.

4. The polymeric resin as claimed in claim 2 in which the recurring monomeric units further comprise the units of a second type represented by the general formula

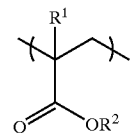

in which $R^1$ is a hydrogen atom or a methyl group and $R^2$ is a tertiary alkyl group having 4 to 20 carbon atoms or a tertiary cycloalkyl group having 4 to 20 carbon atoms.

5. The polymeric resin as claimed in claim 4 of which the molar fraction of the recurring monomeric units of the first type is at least 5%.

6. A photoresist composition which comprises, in the form of a uniform solution:
   (A) the polymeric resin as defined in claim 3 as the base resin;
   (B) a radiation-sensitive acid-generating compound; and
   (C) an organic solvent which dissolves the components (A) and (B).

7. The photoresist composition as claimed in claim 6 in which the radiation-sensitive acid-generating compound as the component (B) is selected from the group consisting of onium salt compounds, alkyl sulfonate compounds, dialkylsulfonyl diazomethane compounds, disulfone compounds and sulfonic acid imides.

8. The photoresist composition as claimed in claim 6 in which the amount of the radiation-sensitive acid-generating compound as the component (B) is in the range from 0.2 to 50 parts by weight per 100 parts by weight of the polymeric resin as the component (A).

9. The photoresist composition as claimed in claim 6 in which the organic solvent as the component (C) is selected from the group consisting of diethyleneglycol dimethyl ether, 1-ethoxy-2-propanol, ethyl lactate, propyleneglycol monomethyl ether acetate and mixtures thereof.

10. A method for the formation of a patterned resist layer on the surface of a substrate which comprises the steps of:
   i) coating the substrate surface with the photoresist composition as defined in claim 6 to form a coating layer of the composition;
   ii) drying the coating layer to form a dried photoresist layer on the substrate;
   iii) patternwise exposing the dried photoresist layer to ultraviolet light having a wavelength not exceeding 300 nm; and
   iv) developing the photoresist layer with an aqueous alkaline developer solution to patternwise dissolve away the photoresist layer.

11. The method for the formation of a patterned resist layer on the surface of a substrate as claimed in claim 10 in which the photoresist layer patternwise exposed to the ultraviolet light in step iii) is subjected to a post-exposure baking treatment prior to development in step iv).

12. The method for the formation of a patterned resist layer on the surface of a substrate as claimed in claim 10 in which the coating layer of the photoresist composition has a thickness in the range from 0.3 to 2.0 µm as dried.

13. The method for the formation of a patterned resist layer on the surface of a substrate as claimed in claim 10 in which the exposure dose to the ultraviolet light is in the range from 0.1 to 200 mJ/cm$^2$.

14. The method for the formation of a patterned resist layer on the surface of a substrate as claimed in claim 11 in which the postexposure baking treatment of the photoresist layer is conducted at a temperature of 60 to 150° C. for 1 to 5 minutes.

15. The method for the formation of a patterned resist layer on the surface of a substrate as claimed in claim 10 in which the aqueous alkaline developer solution used in step iv) is an aqueous solution of tetramethylammonium hydroxide in a concentration of 0.1 to 5% by weight.

* * * * *